United States Patent [19]
Resek et al.

[11] Patent Number: 6,103,911
[45] Date of Patent: Aug. 15, 2000

[54] PROCESS FOR REDUCTION OF (2R)-4-OXOAZETIDINONE-2-CARBOXYLIC ACID

[75] Inventors: James E. Resek, Evanston; Shyamal I. Parekh, Gurnee; Pulla R. Singam, Des Plaines, all of Ill.; Hemant H. Patel, Ahemedabad, India; Michael H. Cain, Grayslake; Bikshandarkoil A. Narayanan, Mundelein, both of Ill.

[73] Assignee: Abbott Laboratories, Abbott Park, Ill.

[21] Appl. No.: 09/333,363

[22] Filed: Jun. 15, 1999

[51] Int. Cl.[7] ............... C07D 205/04; C07D 207/12; C07D 211/76; C07D 213/28

[52] U.S. Cl. .................. 548/950; 546/344; 546/248; 548/570

[58] Field of Search .................... 546/344, 248; 548/570, 950

[56] References Cited

U.S. PATENT DOCUMENTS 3,076,799   2/1963   Testa et al. ..................... 260/239

*Primary Examiner*—Joseph McKane
*Assistant Examiner*—Jane C. Osweeki
*Attorney, Agent, or Firm*—Michael J. Ward

[57] ABSTRACT

The present invention relates to a process for the reduction of an azetidinone-carboxylic acid to an azetidine-alcohol.

25 Claims, No Drawings

PROCESS FOR REDUCTION OF (2R)-4-OXOAZETIDINONE-2-CARBOXYLIC ACID

FIELD OF INVENTION

The present invention relates to a process for the preparation of (2R)-azetidin-2-ylmethanol by the reduction of (2R)-4-oxoazetidinone-2-carboxylic acid.

BACKGROUND OF THE INVENTION

Nicotinic acetylcholine receptor (nAChR) modulators have shown potential as antinociceptive agents. Clinical use of traditional opioid analgesics are limited by a common side effect profile that includes respiratory depression, suppression of gastrointestinal motility, and physical dependence. A non-opioid nAChR modulator, (R)-2-chloro-5-(2-azetidinylmethoxy)pyridine, has been demonstrated to be 30–100 times more potent than morphine and has shown promise as an analgesic agent for use in humans. A key intermediate required for the synthesis of this nAChR modulator is (2R)-azetidin-2-ylmethanol which is synthesized via the reduction of (2R)-4-oxoazetidinone-2-carboxylic acid.

The reduction of (2R)-4-oxoazetidinone-2-carboxylic acid using LiAlH$_4$ in ether (Tetrahedron: Asymmetry 9, 1988, 2791–2794) for the production of (2R)-azetidin-2-ylmethanol is problematic due to the formation of a decomposition product impurity that can not be easily separated from the desired material and the variable yields obtained when this reaction is run on large scale. In addition, reduction using the combination of LiAlH$_4$ and AlCl$_3$ in an ethereal solvent such as tetrahydrofuran (THF) is problematic due to the large exotherm that takes place during the dissolution of AlCl$_3$ in the THF and the production of THF ring-opened byproducts such as chlorobutanol.

SUMMARY OF THE INVENTION

The present invention relates to the reduction of (2R)-4-oxoazetidinone-2-carboxylic acid by reaction with a suitable reducing agent in a mixed solvent system.

DETAILED DISCLOSURE OF THE INVENTION

In one embodiment of the present invention the carboxylic acid and carbonyl functional groups of (2R)-4-oxoazetidinone-2-carboxylic acid (III) are reduced to give (2R)-azetidin-2-ylmethanol (I).

In another embodiment of the present invention, the reduction of (2R)-4-oxoazetidinone-2-carboxylic acid to (2R)-azetidin-2-ylmethanol is carried out using a hydroalane. The hydroalane is formed in-situ by the reaction of LiAlH$_4$ and AlCl$_3$ in a mixture of hydrocarbon and ethereal solvents.

The present invention will be better understood in connection with the following synthetic scheme which illustrates the chemical transformation.

SCHEME 1

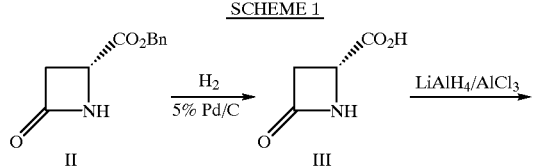

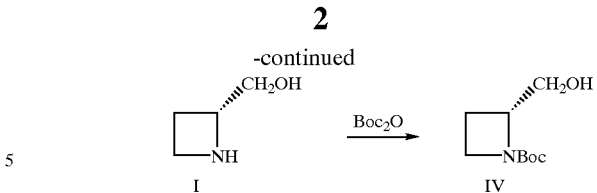

Benzyl (2R)-4-oxoazetidine-2-carboxylate (II) is converted to (2R)-4-oxoazetidine-2-carboxylic acid (III) by treatment with hydrogen in the presence of a catalyst such as 5% palladium on carbon (Org. React., VI, 263–326 (1953)) in a ethereal solvent such as, for example, THF (Tetrahedron Asymmetry, 1988, 9, 2791–2794). (2R)-4-oxo-azetidine-2-carboxylic acid (III) is converted to water soluble (2R) azetidin-2-ylmethanol (I) by reaction with a mixture of hydroalanes in a mixed hydrocarbon/ether solvent system such as hexanes/THF. The preferred reaction temperature for the reduction of III is from about 10° C. to about 55° C. The hydroalanes are formed in-situ by the reaction of LiAlH$_4$ and AlCl$_3$. This reaction is preferably carried out in a mixture of solvents that include a hydrocarbon and ethereal solvent. Without the hydrocarbon solvent to dissipate the heat involved in the dissolution of the LiAlH$_4$ in the ethereal solvent, byproducts of solvent decomposition are a problem. A most preferred solvent system is a mixture of heptanes and THF. Reaction of (2R)azetidin-2-ylmethanol (I) with di-tert-butyl dicarbonate provides the tert-butyl (2R)-2-(hydroxymethyl)-4-oxoazetidine-1-carboxylate (IV).

Definition of Terms

As used throughout this specification and the appended claims, the following terms have the meanings specified.

The term "alkali earth metal ion," as used herein, refers to an ion derived from a metal selected from the group consisting of lithium, sodium, potassium, rubidium and cesium, and the like. Preferred alkali earth metal ions are lithium, sodium, and potassium.

The term "alkoxy," as used herein, refers to an alkyl group, as defined below, attached to the parent molecular moiety through an oxygen atom. Examples of alkoxy groups include, but are not intended to be limited to, methoxy, ethoxy, n-propoxy, iso-propoxy, iso-butoxy, tert-butoxy, and the like. Preferred alkoxy groups are iso-propoxy, iso-butoxy, and tert-butoxy.

The term "alkoxyalkoxy," as used herein, refers to an alkoxy group, as defined above, attached to the parent molecular moiety through an alkoxy group. Examples of alkoxyalkoxy groups include, but are not intended to be limited to, methoxymethoxy, 2-methoxyethoxy, 2-ethoxyethoxy, and the like. Preferred alkoxy groups are methoxymethoxy and 2-methoxyethoxy.

The term "alkyl," as used herein, refers to a monovalent group derived from a straight or branched chain saturated hydrocarbon of one to ten carbon atoms by the removal of a single hydrogen atom. Examples of alkyl groups include, but are not intended to be limited to, methyl, ethyl, n-propyl, iso-propyl, n-butyl, sec-butyl, iso-butyl and tert-butyl, and the like. Preferred alkyl groups are methyl, ethyl, iso-propyl, and tert-butyl.

The term "aryl," as used herein, refers to a mono- or bicyclic carbocyclic ring system having one or two aromatic rings. Preferred aryl groups are phenyl and naphthyl.

The term "ethereal solvent," as used herein, refers to a solvent having the formula $R^4OR^5$ wherein $R^4$ and $R^5$ are independently alkyl or aryl groups as defined above or $R^4$ and $R^5$ together with the oxygen to which they are attached form a heteroalkyl ring as defined above of four to five carbons. Preferred ethereal solvents are diethylether and tetrahydrofuran.

The term "hydroalane," as used herein, refers to any of the aluminum species obtained from the reaction of LiAlH$_4$ and AlX$_3$, wherein X is a halogen. Examples of hydroalanes include, but are not intended to be limited to, a single component or mixtures of AlCl$_2$H, AlClH$_2$, and AlH$_3$.

The term "heteroalkyl ring," as used herein, refers to a five, six, or seven membered ring containing one, two, or three heteroatoms independently selected from the group consisting of nitrogen, oxygen and sulfur.

The term "heptanes" refer to a single component compound or a mixture of isomeric compounds with the formula C$_7$H$_{16}$. For example, heptanes would include a single component or mixtures of n-heptane, 2-methylhexane, 3-methylhexane, 2,2-dimethylpentane, 2,2,3-trimethylbutane, and the like.

The term "hexanes" refer to a single component compound or a mixture of isomeric compounds with the formula C$_6$H$_{14}$. For example, hexanes would include a single component or mixtures of n-hexane, 2-methylpentane, 3-methylpentane, 2,2-dimethylbutane, 2,3-dimethylbutane, and the like.

The term "hydroalane" or "hydroalanes," as used herein, refers to any of the aluminum species obtained from the reaction of LiAlH$_4$ and AlCl$_3$. Examples of hydroalanes include, but are not intended to be limited to, a single component or mixtures of AlCl$_2$H, AlClH$_2$, and AlH$_3$.

The term "hydrocarbon solvent," as used herein, refers to a single compound or a mixture of compounds having the formula C$_p$H$_{2p+2}$ wherein p is 5–10. Examples of hydrocarbon solvents include, but are not intended to be limited to, pentane, n-hexane, 2-methylpentane, 3-methylpentane, 2,2-dimethylbutane, n-heptane, 2-methylhexane, 3-methylhexane, and the like. Preferred hydrocarbon solvents are heptanes and hexanes, as defined below.

The term "mixed solvent system," as used herein, refers to a mixture of two or more solvents.

The term "nonanes," as used herein, refers to a single component compound or a mixture of isomeric compounds with the formula C$_9$H$_{20}$. For example, nonanes would include a single component or mixtures of n-nonane, 2-methyloctane, 3-methyloctane, 4-methyloctane, 2,2-dimethylheptane, 3,3-dimethylheptane, 2,2,3,3-tetramethylpentane, and the like.

The term "octanes" as used herein, refers to a single component compound or a mixture of isomeric compounds with the formula C$_8$H$_{18}$. For example, octanes would include a single component or mixtures of n-octane, 2-methylheptane, 3-methylheptane, 4-methylheptane, 2,2-dimethylhexane, 2,2,3,3-tetramethylbutane, and the like.

The term "pentanes" as used herein, refers to a single component compound or a mixture of isomeric compounds with the formula C$_5$H$_{12}$. For example, pentanes would include a single component or mixtures of n-pentane, 2-methylbutane, 2,2-dimethylpropane, and the like.

The term "reducing agent," as used herein, refers to a reagent that causes the reduction of an organic molecule (see *Advanced Organic Chemistry Third Edition*, Jerry March, John Wiley & Sons, 1985, p. 1048 for a discussion of the reduction of organic molecules).

Abbreviations

Abbreviations which have been used in the descriptions of the scheme and the examples that follow are: Boc for tert-butoxycarbonyl, THF for tetrahydrofuran, LAH for lithium aluminum hydride, Bn for benzyl, lbs for pounds, gal for gallons, L for liters, g for grams, and kg for kilograms.

Synthetic Methods

The compounds and processes of the present invention will be better understood in connection with the following examples, which are intended as an illustration of and not a limitation upon the scope of the invention.

EXAMPLE 1 tert-butyl (2R)-2-(hydroxymethyl)-4-oxoazetidine-1-carboxylate (2R)-4oxoazetidine-2-carboxylic acid A solution of benzyl (2R)-4-oxoazetidine-2-carboxylate (20.1 kg, 98.05 mol) in THF (201 L) was added to Pd/C (1.005 kg) in a 100 gallon hydrogenation reactor. The reaction mixture was stirred under hydrogen (24–26 psi) at 21–24° C. until thin layer chromatography (hexane/ethyl acetate, 1:1) showed disappearance of starting material (8 hours). The mixture was filtered to provide a solution of (2R)-4-oxoazetidine-2-carboxylic acid in THF.

$^1$H NMR (DMSO-d$_6$) δ 8.28 (br, 1H), 4.03 (dd, J=5.9, 2.6 Hz), 3.19 (ddd, J=14.5, 5.8, 1.4 Hz), 2.83 (ddd, J=14.6, 2.6, 1.7 Hz).

(2R)-azetidin-2-ylmethanol

Aluminum chloride (17.52 kg, 131.39 mol) and heptane (40 gal) were charged to a 200 gal reactor. The mixture was cooled to −20° C. and THF (12 gal) was charged, maintaining the temperature below 2–8° C. THF (45 gal) was charged to a separate 100 gal reactor and cooled to −20° C. and lithium aluminum hydride (10 kg, 263.5 mol) was charged and allowed to dissolve slowly by stopping the agitation and maintaining the temperature between 2–16° C. The solution of lithium aluminum hydride in THF was charged to the suspension of aluminum chloride in heptane and THF, maintaining the temperature below 25° C. and the mixture was allowed to stir at 22° C. for 30 min. The solution of (2R)-4-oxoazetidine-2-carboxylic acid in THF from above was charged over a period of about 3 hours, while maintaining the temperature below 30° C. The contents were warmed to 38–44° C. over a period of 30 minutes and maintained at that temperature for 4 hours. The mixture was cooled to 0–10° C. and quenched with 18% aqueous sodium sulfate (16.4 Kg in 20 gal of water) while maintaining the temperature below 30° C. to provide a solution of (2R)-azetidin-2-ylmethanol.

$^1$H NMR (CDCl3) δ 4.49–4.40 (br, 1H), 3.90–3.68 (br m, 4H), 2.23–2.11 (m, 1H), 1.99–1.87 (br, 1H), 1.44 s, 9H).

Tert-butyl (2R)-2-(hydroxymethyl)-4-oxoazetidine-1-carboxylate

Triethylamine (115 lbs) followed by di-tert-butyl dicarbonate (55 lbs, 24.95 kg, 114.31 mol) were charged to the solution of (2R)-azetidin-2-ylmethanol described above. The mixture was allowed to stirr overnight. The contents were centrifuged and the salt cake was washed with ethyl acetate (20 gal). The combined liquors were charged back to a 200 gal reactor and N,N-dimethylethylene-diamine (16.4 L, 13.17 kg, 149.40 mol) was added and the mixture was stirred at room temperature for 1 hour. The solvent was removed by distillation under vacuum and ethylacetate (68 gal) was charged to the residue. The solution was washed with 16.5% aqueous citric acid solution (2×135 kg) and 13.5% sodium bicarbonate solution (116 kg). The solvent was removed by distillation under vacuum at ≦52° C. to give a viscous oil (11.4 kg, potency 64%).

What is claimed is:

1. A process for preparing a compound having formula X,

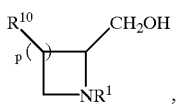

X wherein $R^1$ is hydrogen, $R^{10}$ is selected from the group consisting of hydrogen, alkyl, or aryl, and p is 1–3, which comprises reacting a compound of formula XI,

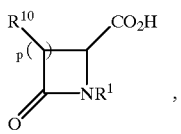

XI with a reducing agent in the presence of a mixed solvent system.

2. A process for preparing a compound having formula XII,

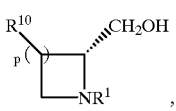

XII wherein $R^1$ is hydrogen, $R^{10}$ is selected from the group consisting of hydrogen, alkyl, or aryl, and p is 1–3, which comprises reacting a compound of formula XIII,

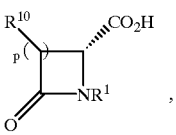

XIII with a reducing agent in the presence of a mixed solvent system.

3. A process for preparing a compound having formula I,

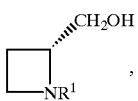

I wherein $R^1$ is hydrogen which comprises reacting (2R)-4-oxoazetidine-2-carboxylic acid with a reducing agent in the presence of a mixed solvent system.

4. A process of claim 3 wherein the reducing agent is selected from the group consisting of $MAl(H)_n(R^2)_m$, $Al(H)_o(R^3)_q$, and hydroalanes, wherein
   $R^2$ is selected from the group consisting of alkyl, alkoxy, and alkoxyalkoxy;
   $R^3$ is alkyl or alkoxy;
   M is an alkali earth metal ion;
   n and m are 0–4;
   n+m is 4;
   o and q are 1–2;
   and o+q is 3;
   with the proviso that n is not 4.

5. A process of claim 4 wherein the reducing agent is $AlH(iso-butyl)_2$ or a hydroalane.

6. A process of claim 5 wherein the reducing agent is a hydroalane.

7. A process of claim 3 wherein the mixed solvent system is a mixture of hydrocarbon and ethereal solvents.

8. A process of claim 7 wherein the hydrocarbon solvent is selected from the group consisting of pentanes, hexanes, heptanes, octanes, and nonanes.

9. A process of claim 8 wherein the hydrocarbon solvent is heptanes.

10. A process of claim 7 wherein the ethereal solvent is selected from the group consisting of tetrahydrofuran, diethylether, and 1,2-dimethoxyethane.

11. A process of claim 10 wherein the ethereal solvent is tetrahydrofuran.

12. A process of claim 3 wherein the reaction is maintained at a temperature of about −10° C. to about 75° C.

13. A process of claim 3 wherein the reaction is maintained at a temperature of about 0° C. to about 65° C.

14. A process of claim 3 wherein the reaction is maintained at a temperature of about 10° C. to about 55° C.

15. A process of claim 6 wherein the hydroalane is produced by the reaction of $LiAlH_4$ and $AlCl_3$.

16. A process of claim 15 wherein the hydroalane formation comprises:
   a) forming a suspension of $AlCl_3$ in a hydrocarbon solvent;
   b) adding an ethereal solvent to said suspension while maintaining a first reaction temperature and;
   c) reacting the mixture formed in part b with $LiAlH_4$ while maintaining a second reaction temperature.

17. A process according to claim 16 wherein the first and second reaction temperatures are between about −15° C. to about 75° C.

18. A process according to claim 16 wherein the first and second reaction temperatures are between about 0° C. to about 60° C.

19. A process according to claim 16 wherein the first and second reaction temperatures are between about 10° C. to about 50° C.

20. A process of claim 16 wherein the hydrocarbon solvent is selected from the group consisting of pentanes, hexanes, heptanes, octanes, and nonanes.

21. A process of claim 20 wherein the hydrocarbon solvent is heptanes.

22. A process of claim 16 wherein the ethereal solvent is selected from the group consisting of tetrahydrofuran, diethylether, and 1,2-dimethoxyethane.

23. A process of claim 22 wherein the ethereal solvent is tetrahydrofuran.

24. A process of claim 16 wherein the molar ratio of $LiAlH_4$ to $AlCl_3$ is between 3:1 and 1:1.

25. A process of claim 24 wherein the molar ratio of $LiAlH_4$ to $AlCl_3$ is between 2:1 and 1:1.

* * * * *